United States Patent [19]

Uchiyama et al.

[11] Patent Number: 4,958,639

[45] Date of Patent: Sep. 25, 1990

[54] ULTRASONIC THERAPEUTICAL APPARATUS

[75] Inventors: Naoki Uchiyama, Hachiogi, Japan; Akio Nakada, Garden City Park, N.Y.; Akihiro Taguchi, Hamburg, Fed. Rep. of Germany; Shinji Hatta; Syuichi Takayama; Takashi Tsukaya; Sakae Takehana; Naomi Sekino; Masaaki Hayashi, all of Hachioji, Japan

[73] Assignee: Olympus Optical Co., Ltd., Japan

[21] Appl. No.: 434,569

[22] Filed: Nov. 8, 1989

Related U.S. Application Data

[63] Continuation of Ser. No. 106,498, Oct. 8, 1987, abandoned.

[30] Foreign Application Priority Data

| Oct. 29, 1986 | [JP] | Japan | 61-257524 |
| Oct. 30, 1986 | [JP] | Japan | 61-259331 |
| Nov. 26, 1986 | [JP] | Japan | 61-282979 |
| Nov. 26, 1986 | [JP] | Japan | 61-280980 |

[51] Int. Cl.$^5$ .................... A61B 8/14; A61B 17/22
[52] U.S. Cl. ................... 128/660.03; 128/24 A
[58] Field of Search ............ 128/660.03, 24 A; 606/127, 128

[56] References Cited

U.S. PATENT DOCUMENTS

| 4,149,419 | 4/1979 | Connell, Jr. et al. | 128/660.1 |
| 4,526,168 | 7/1985 | Hassler et al. | 128/328 |
| 4,617,931 | 10/1986 | Dory | 128/328 |
| 4,763,652 | 8/1988 | Brisson et al. | 128/328 |

FOREIGN PATENT DOCUMENTS

| 0131653 | 1/1985 | European Pat. Off. | |
| 3122056 | 12/1982 | Fed. Rep. of Germany | 128/328 |
| 3328039 | 2/1985 | Fed. Rep. of Germany | 128/328 |
| 2140693 | 12/1984 | United Kingdom | 128/328 |

OTHER PUBLICATIONS

Martin et al., "Ultrasound Stone Localization for Extracorporeal Shock Wave Lithotripsy", British Journal of Urology, 1986, pp. 349–352.

Primary Examiner—Ruth S. Smith
Attorney, Agent, or Firm—Ostrolenk, Faber, Gerb & Soffen

[57] ABSTRACT

An ultrasonic therapeutical apparatus observes the interior of a living body utilizing an ultrasonic wave, allows a location signal to be generated on the basis of an output from the observation system, and controls a focus shifting system in accordance with the location signal. Subsequently, a shock wave generating system is driven to generate an ultrasonic shock wave, which is directed to a focal point, thereby crushing a calculus.

13 Claims, 10 Drawing Sheets

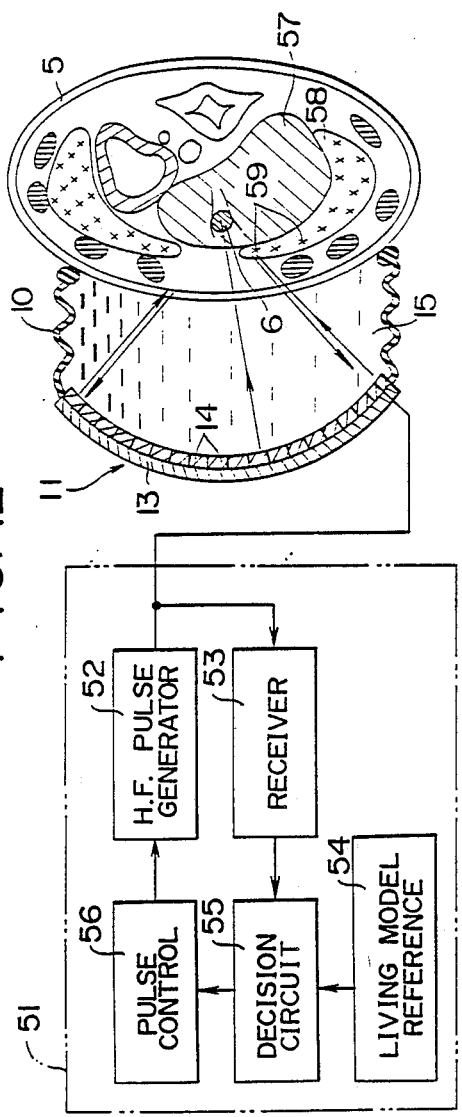
F I G. 12
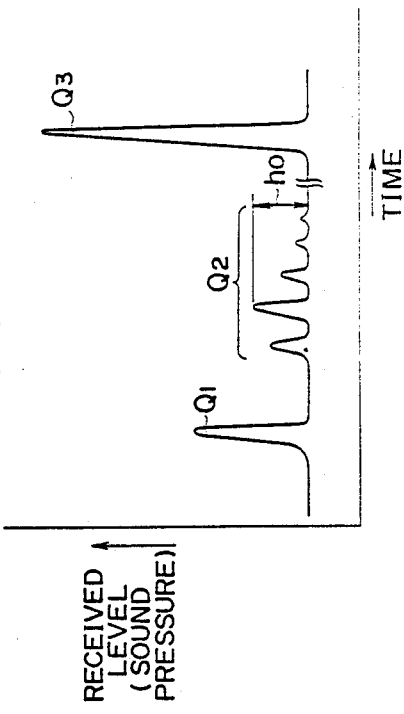
F I G. 13

ULTRASONIC THERAPEUTICAL APPARATUS

This is a continuation of Application Ser. No. 07/106,498 filed on Oct. 8, 1987 now abandoned.

FIELD OF THE INVENTION AND RELATED ART STATEMENT

The invention relates to an ultrasonic therapeutical apparatus, and more particularly, to such apparatus which is used to effect a therapeutical operation by focussing an ultrasonic wave, generated externally, upon a site to be treated.

An apparatus for crushing calculi which operates as an ultrasonic therapeutical apparatus is known (see FR 2556582Al). Generally, a shock wave generator comprising a plurality of ultrasonic vibrators, each formed by a piezoelectric element and disposed in a mosaic pattern around a spherical surface, is disposed in contact with a human body with a water bag which is filled with water or the like interposed therebetween. An ultrasonic shock wave generated by the vibrators is focussed upon a calculus to be removed which exists within a kidney or liver in order to crush such calculus. The ultrasonic shock wave is generated in response to the application of pulse voltage from a shock wave generator circuit to the ultrasonic vibrators.

An ultrasonic recognition apparatus is employed to identify the location of the calculus. An apparatus is also known which includes an acoustical lens or lens system disposed within a liquid for controlling the focussing so that a calculus within a living body may be destroyed in a non-contact manner (see EP 0131653Al).

In the prior art arrangements, no tracking of the calculus has been performed. Accordingly, movements of the calculi as a result of aspiration cause a reduced hit rate of the shock waves. Therefore, where a plurality of calculi are to be crushed, a first one of the calculi must be initially focused upon and crushed. Then a second calculus must be focussed upon and destroyed. Thus, the problem of the movements of the calculi has in the past only been solved by a troublesome procedure. Finally, it has been difficult to crush a coral calculus because of the inability to designate the location where the crushing operation is to be initiated.

In the therapy of hepatolithiasis or lithiasis of renal pelvis, pulmonary alveolus or alveolar sag may be present between the calculus and the ultrasonic vibrator or vibrators. If the calculus crushing operation is directly applied, a differential acoustical impedance between the physical body and the air may result in a reflection from or an attenuation at the location of the pulmonary alveolus of the ultrasonic shock wave, preventing an effective use of the shock wave or causing a likelihood of producing hematoma in the pulmonary alveolus.

An ultrasonic observation system which is generally used in an ultrasonic therapeutical apparatus, for detecting the location of a calculus within a physical body, comprises a probe including an array of ultrasonic vibrators, which are known in themselves. The plurality of vibrators are sequentially activated in one direction at a high rate to scan a single plane, thus detecting the presence of a calculus. The result of such scan is immediately displayed on a display unit such as a display unit including CRT. Thus, by moving the probe along the surface of the physical body to shift the scan plane successively, any calculus which may be present within the kidney or liver may be imaged on the display unit, thus facilitating the detection of the calculus. However, in the ultrasonic observation system described, the probe only scans within a single plane, and if the kidney or other organ moves as a result of aspiration, the calculus may move simultaneously, disappearing from the display screen and frustrating the tracking operation for tracking the calculus.

SUMMARY OF THE INVENTION

In view of the foregoing, it is an object of the invention to provide an ultrasonic therapeutical apparatus which provides for impingement of the shock wave upon a calculus in a positive manner and which is capable of efficiently crushing a plurality of calculi as well as a larger calculus such as a coral calculus.

It is another object of the invention to provide an ultrasonic therapeutical apparatus which enables an ultrasonic crushing of the calculus at a location which is away from the pulmonary alveolus.

It is a further object of the invention to provide an ultrasonic therapeutical apparatus which allows an ultrasonic wave generated by an ultrasonic probe to track a movement of the calculus.

In accordance with the invention, observation means detects the location of a calculus, and a crushing procedure is determined by a location signal generating means. Accordingly, calculi are automatically and successively tracked to allow the crushing operation to be performed after the recognition of the location of each calculus. This assures that the shock wave hits the calculus, allowing a plurality of calculi or a coral calculus to be efficiently crushed. Also in accordance with the invention, a determination is initially rendered to see if a pulmonary alveolus is present within the field of an ultrasonic wave. Only those ultrasonic wave vibrators which are not aimed at the pulmonary alveolus are activated to generate a shock wave, thus achieving an efficient use of the ultrasonic energy while simultaneously providing an ultrasonic therapy with enhanced safety which avoids the location of the pulmonary alveolus.

Finally, the ultrasonic probe is moved in accordance with the movement of the calculus to permit a tracking operation, thus keeping the calculus in its field of view.

BRIEF DESCRIPTION OF THE DRAWINGS

FIG. 12 is a block diagram of an ultrasonic therapeutical apparatus according to another embodiment of the invention;

FIG. 13 graphically shows the waveform of an input pulse occurring in a receiver circuit of FIG. 1.

DETAILED DESCRIPTION OF PREFERRED EMBODIMENTS

Figure 1:
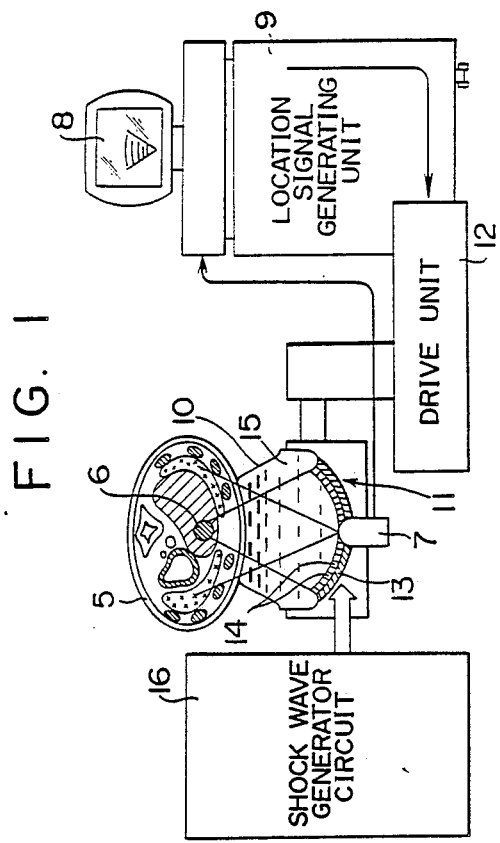
FIG. 1 is a schematic illustration of an ultrasonic therapeutical apparatus according to one embodiment of the invention.
Figure 2:
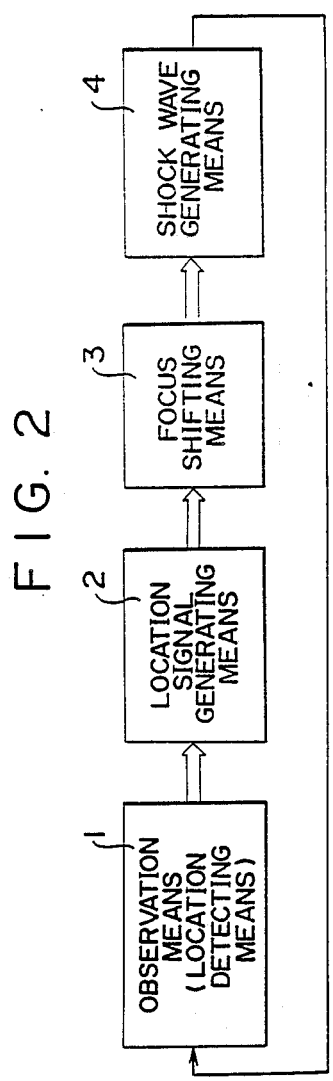
FIG. 2 is a flowchart illustrating the operation of the apparatus shown in FIG. 1.

FIG. 1 illustrates the arrangement of an ultrasonic therapeutical apparatus according to one embodiment of the invention where a human body and part of a shock wave generator are shown in cross section. As shown in FIG. 2, the apparatus essentially comprises observation means 1 which detects the location of an area such as a calculus to be treated within a physical body, location signal generating means 2, focus shifting means 3 and shock wave generating means 4 which generates a shock wave for crushing a calculus.

The observation means 1 comprises an observation unit 7 which emits and directs an ultrasonic wave toward a human body 5 in order to detect the location of a calculus 6 located therein, and a display unit 8 which responds to a detection signal from the observation unit 7 to display the location of the calculus on a display screen such as a CRT.

The location signal generating means 2 comprises a location signal generating unit 9 which sets up a marker at a point on the screen of the display unit 8 and produces a signal applied to the focus shifting means 3 or water bag drive means (drive unit 12) so that the shock wave which is used for the crushing operation is focussed upon the marker. Thus, the location signal generating unit 9 assists in the processing of an image of a detected calculus in a manner to be described later. Specifically, an operator such as a physician may recognize the size or the number of calculus or calculi displayed and determine a crushing procedure to establish the sequence in which a plurality of calculi are sequentially crushed beginning with the biggest one, for example, or the sequence in which various parts of a coral calculus are crushed in a sequential manner. To this end, the apparatus 9 provides a signal relating to such crushing procedure as well as a signal which would provide a most effective treatment, which is entered upon the display screen as by a light pen. Such signal is used to change the focal point of the shock wave, which may be required because of a displacement of the focus as a result of the crushing operation, and which is determined by detecting the location and the size of the calculus periodically. Such signals are stored for use in providing a location signal which is supplied to the water bag drive means during a next crushing operation.

The focus shifting means 3 or water bag drive means comprises a drive unit 12 which is effective to move a water bag 10 and a shock wave generator 11, to be described later, as by a device controlled in accordance with the location signal. Specifically, the shock wave generator 11 comprises a plurality of ultrasonic vibrators 14, formed by piezoelectric elements, which are mounted on and secured to a front surface of a mounting plate 13 having a spherical surface so as to define a mosaic pattern, the elements being disposed so that a shock wave front is directed toward the human body 5. The water bag 10 which is interposed between the shock wave generator 11 and the body 5 is formed of a soft resin material and includes liquid injection and pressure control means. The bag 10 is filled with water, for example, or other shock wave transmitting liquid 15.

The shock wave generating means 4 comprises the shock wave generator 11 mentioned above and a shock wave generator circuit 16 such as an ultrasonic pulse voltage generator circuit which is known in itself, the circuit 16 driving the ultrasonic vibrators 14.

FIG. 2 shows a sequence of operation of the ultrasonic therapeutical apparatus constructed in the manner mentioned above. Thus, the location of a calculus within a physical body is initially detected by the observation means 1, and an analysis of the status of the calculus which is recognized by the observation means 1 is made within the location signal generating means. An operator such as a physician selects and determines an optimum treatment depending on the kind of the calculus detected, and the crushing procedure as well as the location signal are stored. The location signal is applied to the focus shifting means 3 to drive the water bag 10 and the shock wave generator 11 so that the shock wave is focussed upon the calculus. Subsequently, the shock wave generating means 4 generates a shock wave, which destroys the calculus. After a given number of shock waves have been generated, the described operation is temporarily stopped in order to confirm the size of fragments of the calculus and the focal position of the shock wave. Subsequently, the above operation is repeated until the calculus is completely crushed.

Figure 3:
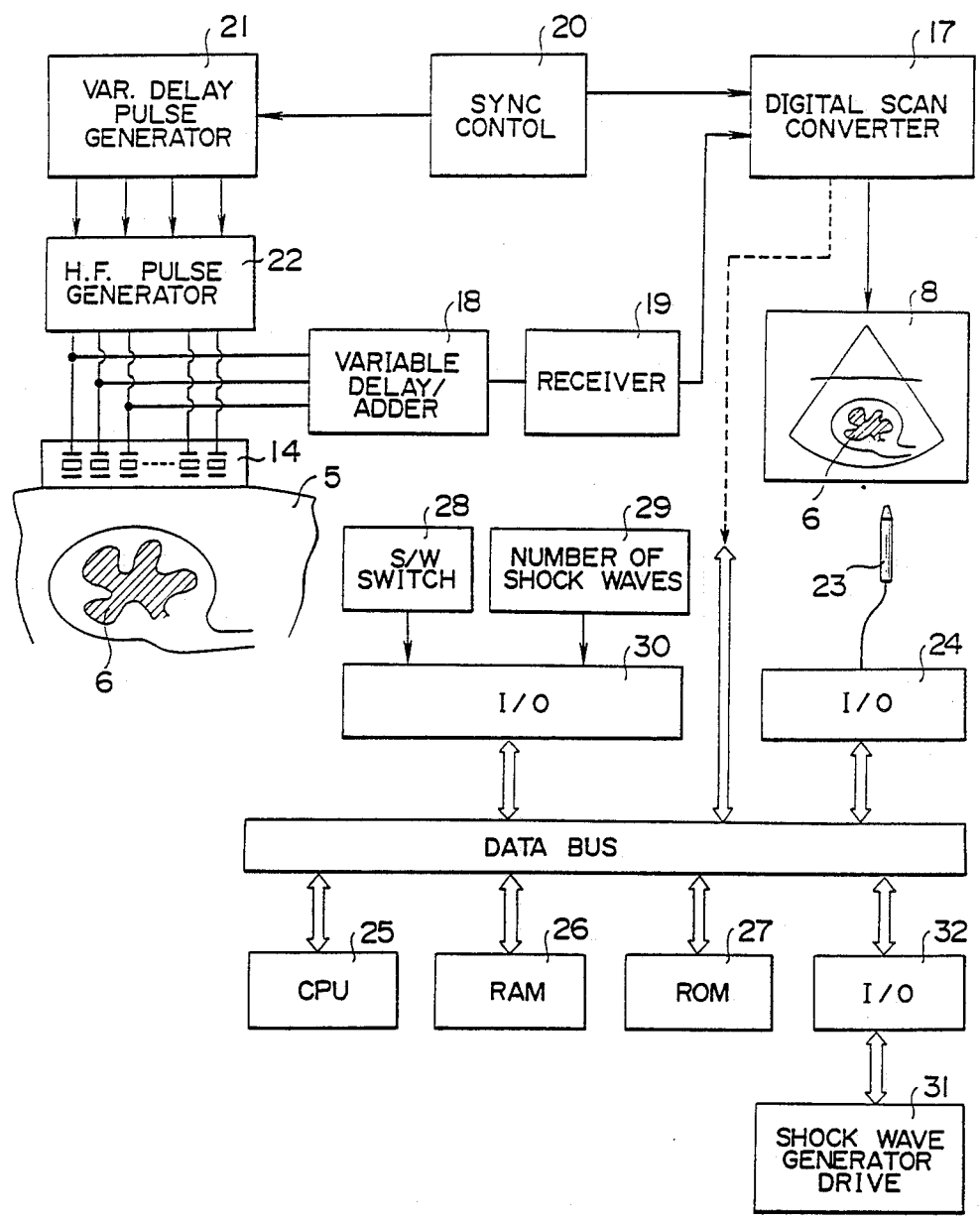
FIG. 3 is a block diagram of essential components of the apparatus shown in FIG. 1.

FIG. 3 is a block diagram showing essential parts of the ultrasonic therapeutical apparatus. A digital scan converter 17 supplies a calculus position signal to the monitor display unit 8, which displays it graphically. A signal from the ultrasonic vibrator 14 detecting the calculus 6 located within the physical body 5 is also fed to the converter 17 through an analog variable delay-/adder 18 and a receiver 19. A digital variable delay pulse generator 21 is synchronized with the converter 17 by means of a synchronization control circuit 20, and causes a signal from a high frequency pulse generator 22 to be applied to the ultrasonic vibrator 14. In the present instance, the ultrasonic vibrator 14 comprises an element in the form of a flat plate, and hence the delay pulse generator 21 is used to provide a pulse delay for purpose of focussing operation.

A location signal which is entered upon the display unit 8 as by the light pen 23 is fed through I/O port 24 and data bus to a control memory which comprises CPU 25, RAM 26 and ROM 27 for storage therein, thus allowing a subsequent output therefrom. The control memory is also connected with a shock wave start switch 28 and a number of shock waves presetting circuit 29 through I/O port 30 and through the data bus. In addition, a shock wave generator drive circuit 31 is connected to the data bus through I/O port 32.

Figure 4:
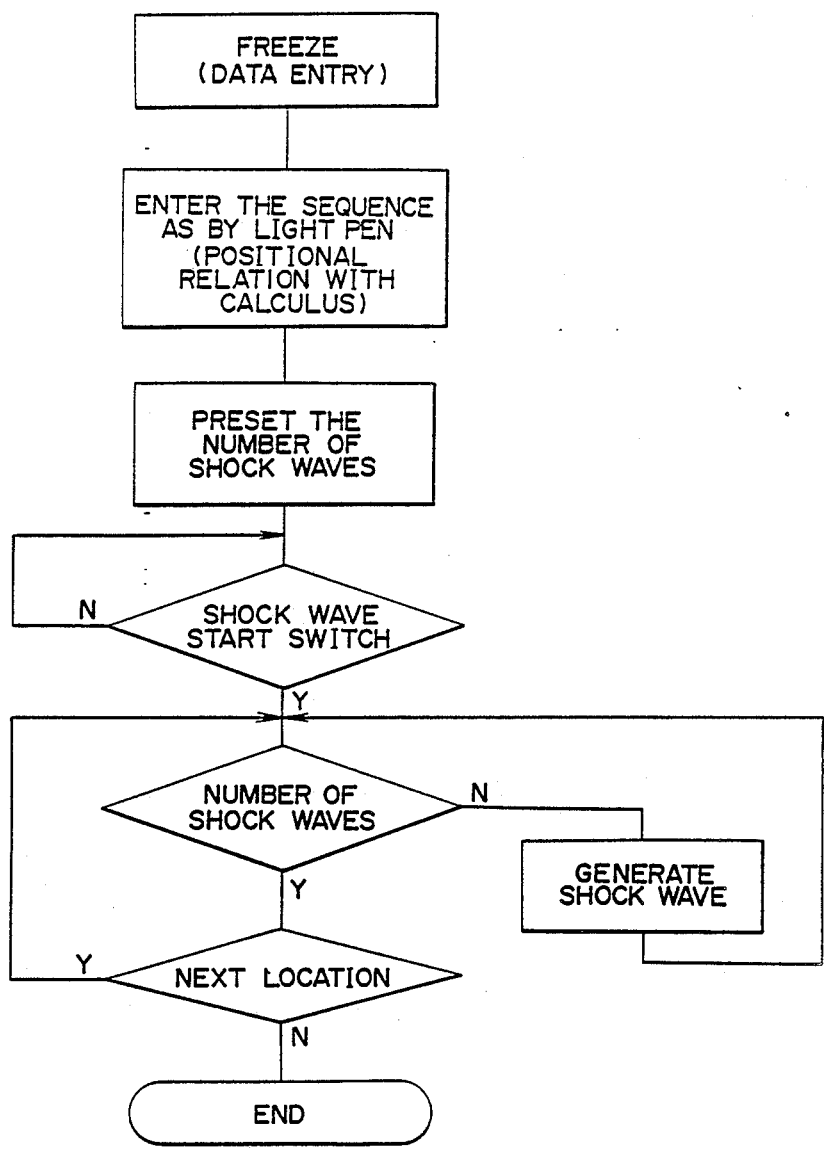
FIG. 4 is a flowchart illustrating the operation of essential components shown in FIG. 3.
Figure 5:
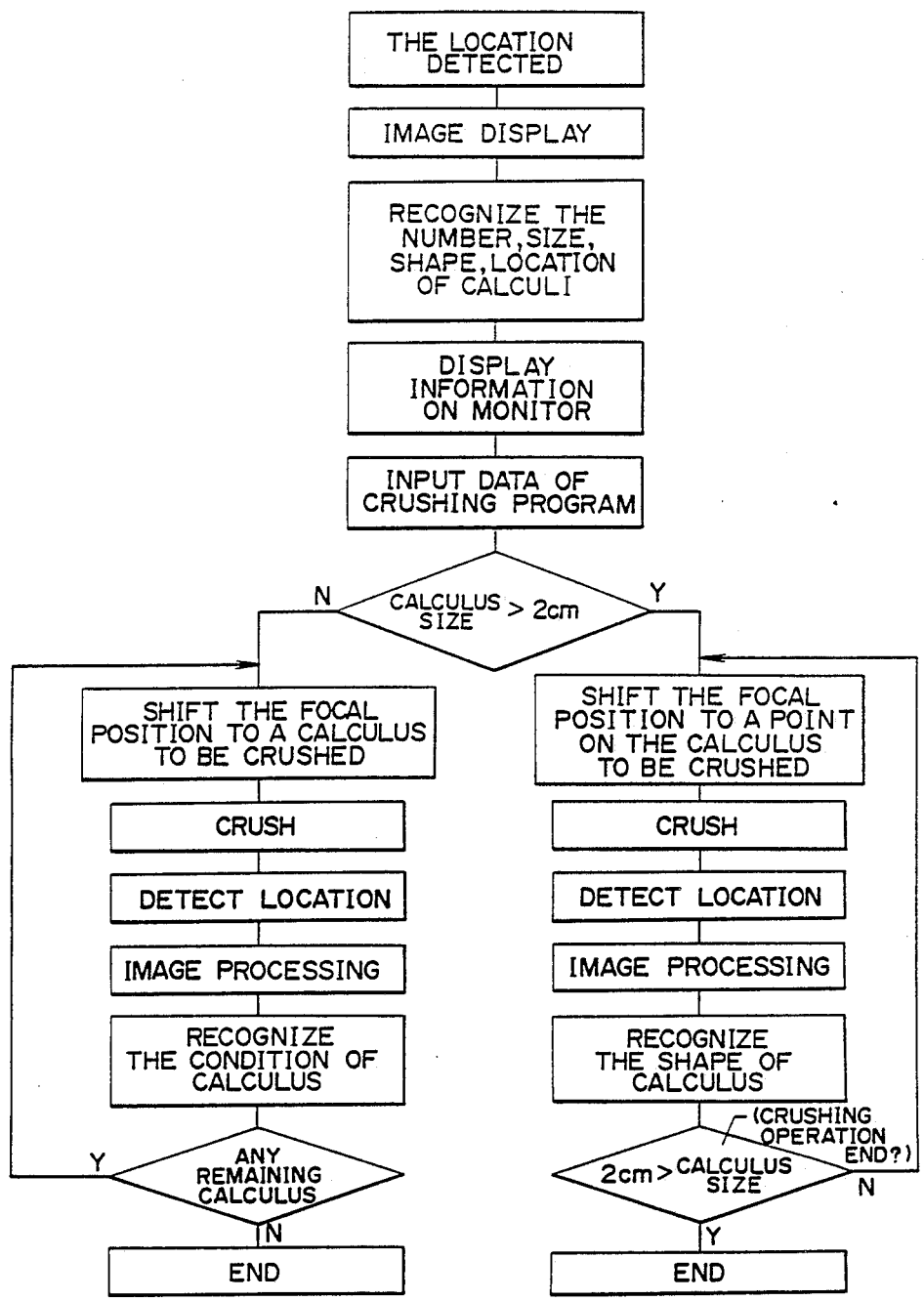
FIG. 5 is a flowchart illustrating a detailed operation of the apparatus shown in FIG. 1.

FIG. 4 is a flowchart illustrating a sequence of operation of various components shown in FIG. 3. Specifically, the apparatus temporarily assumes a freeze condition during the data entry. Using a light pen, for example, the order in which calculi are to be crushed is entered upon the screen of the display unit 8. After presetting the number of shock waves, the start switch may be turned on, whereupon a shock wave is generated and directed to the location of a calculus which is set in the first place in the sequence, and continues to be generated until the given number of shock waves is reached, thus crushing that calculus. Subsequently, a similar crushing operation is repeated upon a calculus which is set in the second place in the sequence. Thus, the successive calculi are sequentially selected and crushed.

Figure 6A:
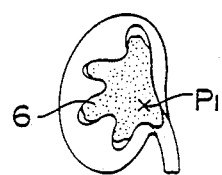
FIGS. 6A to 6F are a series of illustrations of a procedure for crushing a coral calculus.

Referring to FIGS. 5 and 6A to 6F to provide a more detailed description of the operation of the ultrasonic therapeutical apparatus shown in FIG. 1 which includes the components illustrated in FIG. 3, the location of calculus 6 is detected by the observation means 1, which is then subject to imaging processing to allow the number, the size, the shape and the location of a calculus or calculi to be recognized on the screen of the monitor display unit 8. Viewing such calculus information presented on the monitor screen, an operator such as a physician specifies a most efficient sequence in which a plurality of calculi are to be crushed, such as in the order of the size or in the order of the adjacency to the ureter, depending upon the symptoms, using a light pen or the like. At this time, a determination is made to see if the size of a calculus is or is not greater than 2 cm, for example. As indicated in FIG. 6A, if a single coral calculus of a size greater than 2 cm is formed within the kidney, a sequence is specified so that a portion adjacent to the exit from the kidney to the ureter is crushed first. Data representing a crushing sequence specified by means of a light pen in the manner mentioned above is inputted to the location signal generating unit 9.

The operation then proceeds to a crushing operation. The location signal delivered from the location signal generating unit 9 activates the focus shifting means 3, or the drive unit 12 which moves the water bag 10 and the shock wave generator 11, thus shifting the focal position of the generator 11 to the location of the first calculus in the sequence.

Figure 6D:
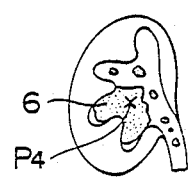
Figure 6B:
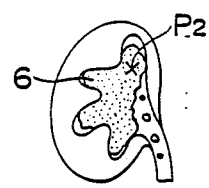
Figure 6E:
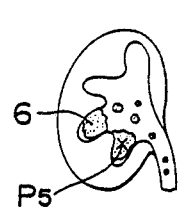
Figure 6C:
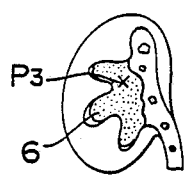
Figure 6F:
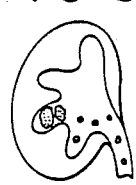

It is to be noted that the location signal which is used when a calculus greater than 2 cm in size is to be crushed is different from the location signal which is used when a plurality of calculi are present.

Where the calculus is coral and has an increased size, the focal position is chosen to be located at position $P_1$ which is close to the exit to the ureter as indicated in FIG. 6A, based on the above data. A crushing operation then follows. When part of the calculus is crushed, the resulting configuration of the calculus is detected by the observation means 1 to determine if the calculus is displaced in response to the shock wave or if the size of the crushed calculus is reduced below 2 cm, by viewing a visual representation on the display screen. If such is the case, the focal position is automatically shifted to position $P_2$ close to the fracture of the calculus as indicated in FIG. 6B, followed by a crushing operation. Upon completion of the second crushing operation which is performed at the position $P_2$, the focal position is sequentially shifted to $P_3$, $P_4$ and $P_5$, as illustrated in FIGS. 6C, 6D and 6E, each time followed by the crushing operation. Finally, the calculus will be crushed to a size less than 2 cm as shown in FIG. 6F, whereby the crushing operation is completed.

In the event the calculus is not reduced to less than 2 cm or the calculus has been displaced as a result of a crushing operation as indicated by the visual representation on the display screen, data entry is renewed for performing a continued crushing operation.

On the other hand, where a plurality of calculi are present, after the focal position is automatically shifted to the location of a first calculus followed by a crushing operation and when the observation means 1 detects that the first calculus has been crushed to a size less than a given value, the focal position is automatically shifted to the location of a second calculus according to the predetermined sequence, thus continuing the crushing operation until the crushing of the calculi is completed.

In the embodiment of the ultrasonic therapeutical apparatus mentioned above, the calculus is continuously and automatically tracked and the location of the calculus is recognized before initiating another crushing operation. This assures a reliable hit of the shock wave upon the calculus, permitting an efficient crushing operation of a plurality of calculi or a bigger calculus such as a coral calculus.

Figure 7B:
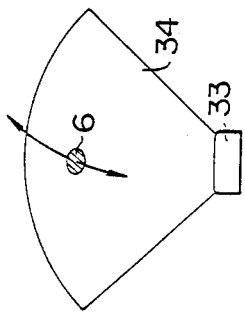
FIGS. 7A and 7B are diagrammatic views of a scan plane of an ultrasonic probe.
Figure 7A:
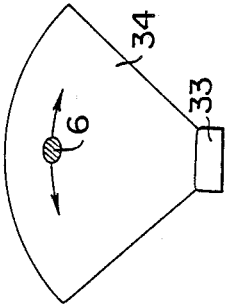
Figure 8:
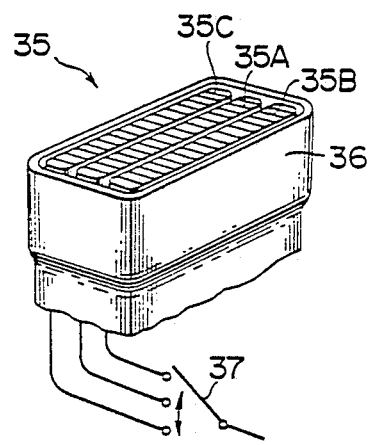
FIG. 8 is a perspective view of one form of ultrasonic probe.

The observation unit 7 includes an ultrasonic probe. As indicated in FIG. 7A, as long as the calculus 6 moves along within the scan plane 34 of the ultrasonic probe 33, it does not disappear from the display screen. However, if it moves in a direction perpendicular to the scan plane 34 or in a direction perpendicular to the surface of the human body, as illustrated in FIG. 7B, it will disappear from the display screen, thus frustrating the tracking operation. To accommodate for this, FIG. 8 shows an ultrasonic probe 35 which enables a tracking of the calculus 6 to be maintained for purpose of observation. The probe 35 comprises an ordinary probe 35A comprising an array of ultrasonic vibrators, and also includes additional probes 35B and 35C which are constructed in an identical manner, all of which are received in a probe casing 36. The application of an operating voltage to the respective probes 35A to 35C is changed by a switch 37. In use, the central probe 35A is normally used for purpose of observation, and if the calculus happens to move out of the plane, the switch 37 is changed in a corresponding manner.

Figure 9:
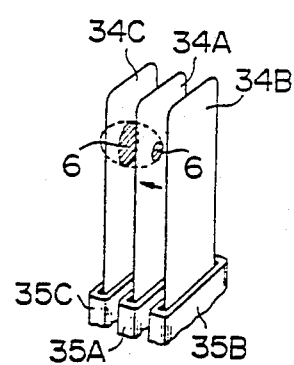
FIG. 9 is a perspective view showing a movement of the scan plane of the ultrasonic probe shown in FIG. 7.

Specifically, FIG. 9 shows that the central probe 35A catches the calculus 6 within its scan plane 34A. If the calculus moves rearwardly or inwardly into the human body, for example, there occurs a change in the area of an image corresponding to the calculus 6. Accordingly, the switch 37 may be changed to operate the rearwardly located probe 35C in response to such change, whereby the calculus 6 can be clearly caught within the scan plane 34C of the rear probe 35C. In this manner, by changing the front, the central and the rear probe 35B, 35A and 35C to track the calculus 6 which may move from time to time, it is possible to acquire the image of the calculus in a reliable manner. It will be seen that an analysis of such tracking data provides the size of the calculus as well as the distance of travel, which can be utilized to focus the shock wave upon the calculus in a positive manner, thus improving the efficiency of the crushing operation.

This arrangement provides an additional advantage. With a conventional ultrasonic observation unit, a probe mounted on the tip thereof comprises a vibrator of a given frequency. The inability to freely choose a frequency results in an inconvenience in achieving a desired observation. With an ultrasonic observation unit applied to the surface of the physical body, the vibrators used are usually of two frequencies, 5 MHz or 3.5 MHz. A vibrator of frequency 5 MHz provides an excellent resolution but suffers from an increased attenuation which stands in the way of observation, due to the thickness of a fat zone of a patient. On the other hand, a vibrator of frequency 3.5 MHz enables an observation of a deep area, but suffers from a rough image. Thus, a high frequency provides excellent resolution, but an observation which is possible with it is limited to a shallow zone close to the surface of the physical body. A low frequency results in a poor resolution, but enables observation of a deep zone. It will then be seen that the use of the ultrasonic probe 35 as mentioned above which permits a switching between a plurality of vibrators, vibrators of different frequencies may be selectively used, thus overcoming the inconvenience of the prior art.

Figure 10:
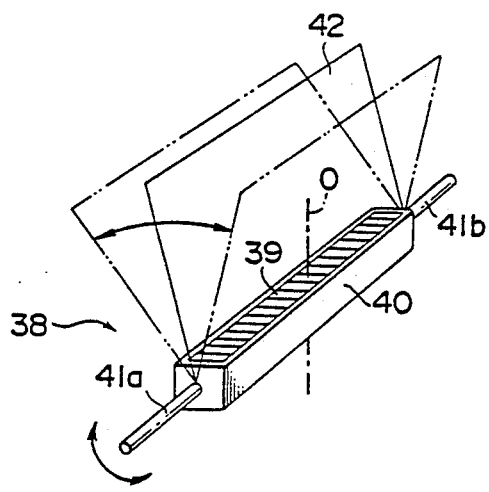
FIGS. 10 and 11 are perspective views of other forms of ultrasonic probe.

FIG. 10 shows another form of ultrasonic probe 38. The probe 38 comprises an array of ultrasonic vibrators 39 which are received in a casing 40 carrying a pair of pivots 41a, 41b, thus allowing a rocking motion of the probe by turning the pivots in a manner indicated by an arrow. This shifts the scan plane 42 back and forth, enabling the tracking of a movement of a calculus.

Figure 11:
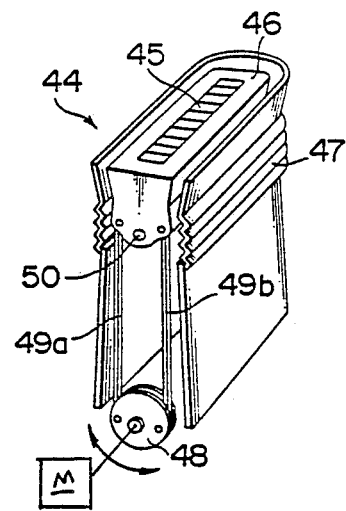

FIG. 11 shows a further form of ultrasonic probe 44 disposed for rocking motion. The probe 44 comprises an array of ultrasonic vibrators which are held within a frame 46, which is in turn disposed within a casing 47. At their lower ends, the opposite sides of the frame 46 are fastened to one end of each of a plurality of connecting strings 49a, 49b, the other ends of which are symmetrically secured to a pulley 48, with the pulley being driven for rotation by a motor M. As the motor is set in motion, the frame 46 may be rocked about its pivot 50, thus oscillating the probe 45 fore and aft to displace the scan plane in a corresponding manner, thus permitting a calculus to be tracked.

Alternatively, a probe comprising an array of ultrasonic vibrators may be rotated about its center axis 0 (see FIG. 10), permitting a stereographic image of the calculus to be obtained.

When a pulmonary alveolus or pulmonary sac is located along a shock wave generated by the shock wave generator 11, it is possible to destroy a calculus while avoiding the pulmonary alveolus. Such an embodiment will now be described with reference to FIGS. 12 and 13.

The ultrasonic vibrator 14 of the ultrasonic generator 11 is connected to an ultrasonic wave control and drive circuit 51, which comprises a high frequency pulse generator circuit 52, a receiver circuit 53 for receiving an output from the generator circuit 52 and for receiving a reflection pulse picked up by the ultrasonic vibrator 14, a decision circuit 55 which compares an output from the receiver circuit 53 against an output from a living body model reference signal generator circuit 54, and a pulse control circuit 56 for controlling the high frequency pulse generator circuit 52 in accordance with an output from the decision circuit 55. It is to be noted that the control and drive circuit 51 is associated with each of the ultrasonic vibrators 14 which form together the shock wave generator 11.

Assuming that a calculus 6 exists within a liver 57 of a physical body 5 as indicated in FIG. 12, it is necessary to focus the ultrasonic shock wave upon the calculus 6 to destroy it. However, as shown, a lung 58 is located close thereto, and hence the shock wave must be emitted so as to avoid the of pulmonary alveolus 59 of the lung 58.

At this end, the high frequency pulse generator circuit 52 of the control and drive circuit 51 emits a high frequency pulse for purpose of observation, which is applied to the ultrasonic vibrator 14. This observation pulse is received by the receiver circuit 53 as a waveform signal $Q_1$ shown in FIG. 13. When the observation pulse is applied to the vibrator 14, it emits an observation ultrasonic wave which is directed to an area of the human body 5 to be treated. The observation ultrasonic wave is then reflected by the body 5, and the reflection wave is transformed into an electrical signal by the vibrator 14, whereby the receiver circuit 53 receives it as a waveform signal $Q_2$ shown in FIG. 13. The level of the waveform signal $Q_2$ 2 which results from the received reflection wave is used to determine the area to be treated. Because of a large difference in the acoustical impedance between the pulmonary alveolus 59 and the remainder of the human body 5 as mentioned above, when the observation ultrasonic wave is reflected from the pulmonary alveolus 59, the resulting signal level will be exceedingly high as compared with the signal level of waves which are reflected from the calculus 6 or the remainder of the physical body. Accordingly, if the level of the waveform signal $Q_2$ exceeds a given value $h_0$, the decision circuit 55 detects the presence of the pulmonary alveolus 59. Thus the living body model reference signal generator circuit 54 is designed to produce a reference signal for a configuration model which corresponds to the internal construction of the living body 5. Accordingly, when the receiver circuit 53 has received a reflected wave, the waveform signal $Q_3$ of which exceeds the value $h_0$, the resulting comparison between the output from the receiver circuit 53 and the reference signal which is made within the decision circuit 55 determines that the presence of the pulmonary alveolus 59 is detected. The decision circuit then provides an output which instructs the pulse control circuit 56 to cease driving the high frequency pulse generator circuit 52. In this manner, the high frequency pulse generator circuit 52 ceases to be driven as long as the pulmonary alveolus 59 is located on the course of the ultrasonic wave. If there is no pulmonary alveolus 59 present on the course of the ultrasonic wave and the presence of the calculus 6 is recognized, an output from the decision circuit 55 controls the pulse control circuit 56 to allow the high frequency pulse generator circuit 52 to initiate the generation of a control signal which is used to generate the shock wave.

As mentioned previously, such operation takes place with each ultrasonic wave control and drive circuit 51 associated with each ultrasonic vibrator 14, and therefore it will be seen that those ultrasonic vibrators 14 having their ultrasonic waves directed toward the calculus 6 on which the pulmonary alveolus 59 is present do not generate a shock wave while the remaining ultrasonic vibrators 14 generate shock waves to destroy the calculus 6. It is possible that when the lung 57 moves due to aspiration, the pulmonary alveolus 59 may move into the course of the ultrasonic wave. In such instance, the generation of the respective ultrasonic vibrators 04 ceases in accordance with a movement of the pulmonary alveolus 59. This enables efficient use of the ultrasonic energy while avoiding the occurrence of a hepatoma in the lung 57.

In the embodiment described above, because reflection of the ultrasonic wave from the pulmonary alveolus 59 is high, the presence of the pulmonary alveolus is detected when an output from the receiver circuit 53 exceeds a given value. However, the pulmonary alveolus generally has a spheroidal configuration, and when the ultrasonic wave impinges upon it, a substantial portion of the reflection will be scattered around it except for the portion which is directed toward the center of the pulmonary alveolus, resulting in a reduced amount of reflection which reaches the ultrasonic vibrator 14. In view of this, the presence of the pulmonary alveolus may be determined when an output from the receiver circuit 53 less than a given value is detected.

In the present embodiment, the ultrasonic vibrator 14 which emits the shock wave also serves as an observation function, but a devoted ultrasonic observation unit 7 (see FIGS. 1 and 2) may be provided as part of the observation means 1 in the manner initially mentioned.

Considering the focus shifting means 3 (see FIG. 2), it usually comprises means for driving the water bag, and accordingly comprises a drive unit 12 (see FIG. 1) which moves the water bag 10 and the shock wave generator 11 in accordance with the location signal. However, an arrangement which moves the water bag 10 and the shock wave generator 11 necessarily results in an increased size of the entire ultrasonic therapeutical apparatus and also requires increased power for the moving unit 12

Figure 14:
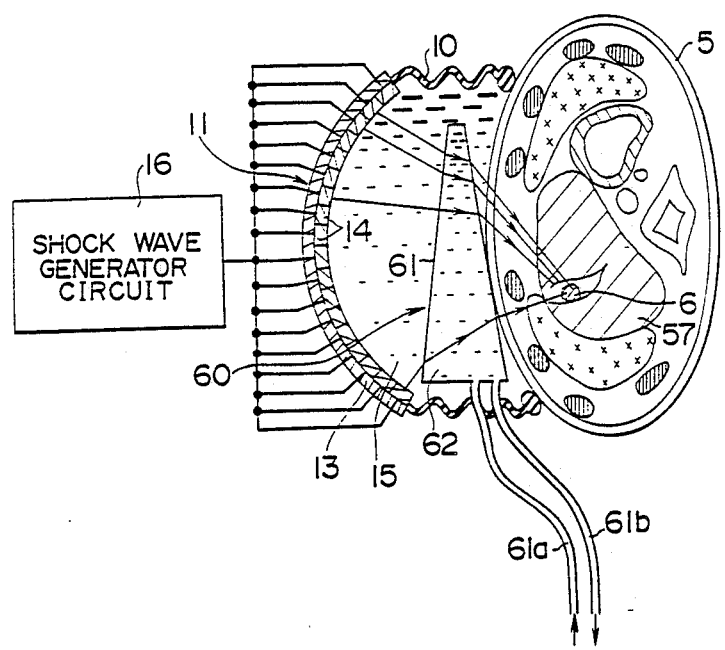
FIGS. 14 to 17 illustrate other forms of means for shifting the focus.

FIG. 14 shows a shock wave inflector 60 disposed within the water bag 10 between the shock wave generator 11 and the human body 5. The inflector 60 comprises a flexible vessel 61 which is filled with a shock wave transmitting liquid 62. The vessel 61 is provided with an injection tube 61a and a displacement tube 61b, which permit the liquid to be injected or discharged for purpose of replacement. The shock wave transmitting liquid 15 contained within the water bag 10 and the shock wave transmitting liquid 62 contained within the inflector 60 have different acoustical impedances. Representing the density of the liquids 15 and 62 by $\rho_1$ and $\rho_2$, respectively, and the transmission velocity of the liquids 15 and 62 by $c_1$ and $c_2$, respectively, the liquid 15 has an acoustical impedance of $\rho_1 c_1$ while the liquid 62 has an acoustical impedance $\rho_2 c_2$. Because different liquids 15, 62 are used, the acoustical impedances $\rho_1 c_1$ and $\rho_2 c_2$ are also different. Accordingly, when a drive pulse is applied from the shock wave generator circuit 16 to the generator 11, the ultrasonic shock wave which is emitted by each of the ultrasonic vibrators 14 will proceed through the liquid 15 in a manner indicated by arrows, and then will be refracted into the inflector 60, subsequently proceeding into the human body 5. Where the calculus 6 exists in the liver 57 of the body 5 as indicated, it is necessary to focus the shock wave upon the calculus 6 in order to destroy it. Accordingly, the focal position where shock waves converge is adjusted by controlling the amount of liquid 62 injected into the vessel 61 of the inflector 60 or choosing the type of liquid 62 to thereby change the acoustical impedance of the liquid, causing a resulting change in the refractive index of the shock wave at the inflector 60. In this manner, the ultrasonic shock wave emitted by the generator 11 may be easily focussed upon the calculus 6 to destroy it. The configuration of the inflector 60 is not limited to the prism form indicated, but various other forms may also be used. The vessels 61 having different forms may be provided, and a selected one of them may be used depending on the location of an area to be treated within the physical body 5. The focal position of the shock wave may also be adjusted by moving the inflector 60 horizontally and/or vertically within the water bag 10. In this manner, the shock wave may be focussed at any desired point without moving the entire apparatus or the shock wave generator 11.

In the focus shifting means illustrated in FIG. 14, a spherical array of ultrasonic vibrators 14 is used to construct the shock wave generator 11, but a flat shape shock wave generator comprising a flat array of ultrasonic vibrators 14 may also be used. It will be understood that a flat shape shock wave generator is much easier to manufacture than the shock wave generator 17 mentioned above. The use of such shock wave generator of a flat form in the focus shifting means will now be described.

Figure 15:
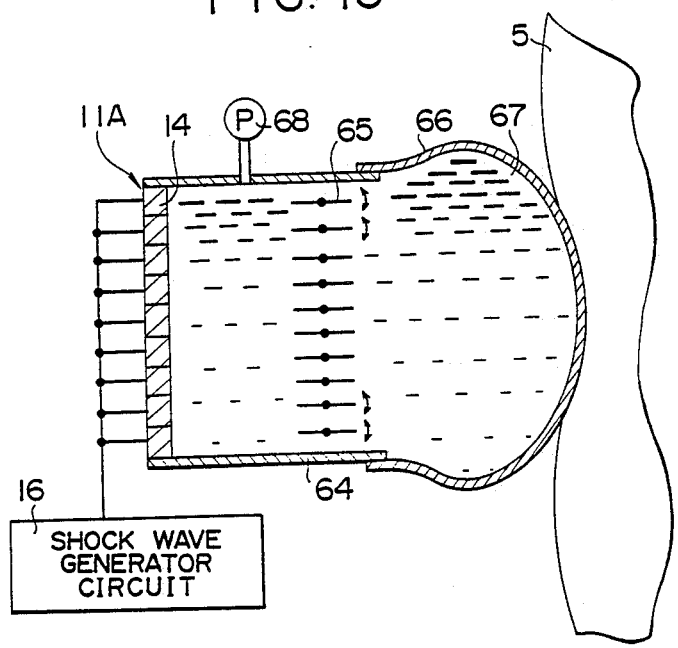

In an embodiment shown in FIG. 15, a shock wave generator 11A of a flat shape comprising a plurality of ultrasonic vibrators 14 is attached to a rear end of a cylinder 64 so as to close the opening thereof. In response to the application of a drive pulse from the shock wave generator circuit 16 to each of the ultrasonic vibrators 14, each vibrator 14 emits an ultrasonic shock wave. An array of vanes 65 is disposed within the cylinder 64 in order to control the travelling direction of the ultrasonic shock waves. Each of such vane 65 may be rotated through a given angle to a tilted position by a stepping motor of an associated controller, not shown. A pouch 66 covers a front opening of the cylinder 64, and a shock wave transmitting liquid 67 fills the internal space defined by the cylinder 64 and the pouch 66. A suitable amount of liquid 67 is injected into the cylinder by a pump 68 connected to the cylinder 64.

In use, the orientation of the individual vanes 65 is adjusted according to the location of an area to be treated within the human body 5. Specifically, when an area to be treated or a calculus 6 (see FIG. 14) is located on the center axis of the shock wave generator 11A, vanes 65 which are located outwardly are tilted to a greater angle while inner vanes 65 are tilted to a smaller angle so that the shock waves from the individual vibrators 64 may be focussed upon a single point on the center axis. The focal position may be varied as desired to be on-center or off-center by adjusting the angles of the individual vanes 65. This facilitates the focussing of the shock wave upon the calculus 6.

In addition to the use of the vanes 65, various means may be used to converge the ultrasonic shock wave upon the area to be treated. Such means are illustrated in FIGS. 16 and 17.

Figure 16:
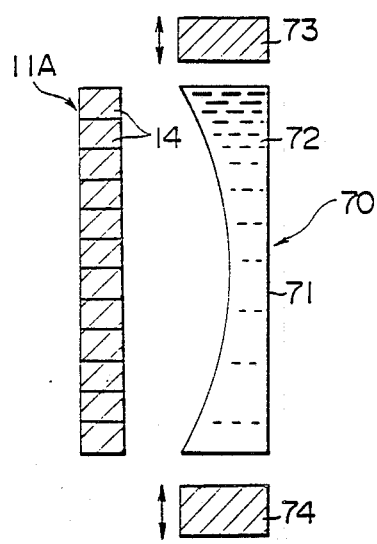

In an embodiment shown in FIG. 16, a shock wave inflector 70 having a flexible vessel 71 in the form of a concave lens and filled with a magnetic fluid 72 is disposed forwardly of the shock wave generator 11A. The magnetic fluid 72 exhibits an acoustical impedance which is different from that of a shock wave transmitting liquid 67 (see FIG. 15) which is distributed around the inflector 70, whereby the ultrasonic shock waves emitted by the individual vibrators 14 have courses which are redirected by the inflector 70 to converge upon a forwardly located point. A pair of magnets 73 and 74 are disposed adjacent to the opposite ends of the inflector 70 and are movable in a direction toward or away from the inflector 70. Thus, by controlling the location of the magnets 73, 74, the magnetic fluid 72 in the vessel 71 may be displaced to change the configuration of the inflector 70, thereby changing the position where the shock waves converge.

Figure 17:
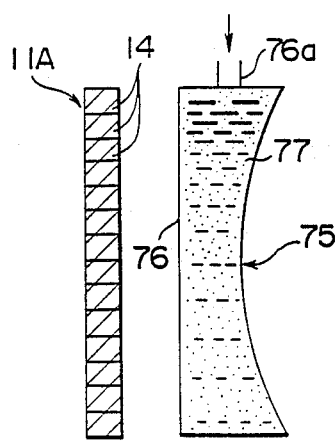

In an embodiment shown in FIG. 17, a shock wave inflector 75 in the form of a concave lens is disposed forwardly of the shock wave generator 11A. The inflector 75 has a vessel 76 in the form of a concave lens which is filled with a shock wave transmitting agent 77 comprising an impurity exhibiting a different acoustical impedance from that of a shock wave transmitting liquid 67 (see FIG. 15) which is distributed around the vessel 76. Again, by changing the amount or kind of the impurity in the agent 77 which is injected through an inlet/outlet 76a into the vessel 76 of the inflector 75, the refractive index of the inflector 75 may be changed, facilitating the focal position of the shock wave to be changed.

What is claimed is:

1. An ultrasonic therapeutic apparatus, comprising:
   (a) observation means for:
      (1) continuously observing an area within a patient's body;
      (2) generating a detection signal upon detection of a calculus located within said area; and
      (3) continuously tracking the location of said calculus within said area;
   (b) means responsive to said detection signal from said observation means for continuously providing a location signal based upon the location of said continuously tracked calculus;
   (c) ultrasonic shock wave generating means for generating an ultrasonic shock wave to crush said calculus, said ultrasonic shock wave generating means including an array of ultrasonic shock wave emitting elements for directing said ultrasonic shock wave toward a focal point to crush said calculus; and
   (d) focal point shifting means for automatically shifting said focal point in accordance with said location signal to crush said calculus; and
   wherein said observation means includes observation wave generating means for generating an ultrasonic observation wave, said ultrasonic observation wave being used to determine the three-dimensional location of said calculus within said area of said patient's body, said observation wave generating means being cooperably associated with said ultrasonic shock wave generating means so that said ultrasonic observation wave and said ultrasonic shock wave are generated from substantially the same location.

2. An ultrasonic therapeutic apparatus as recited in claim 1, wherein said observation means includes means for detecting a pulmonary alveolus, and for controlling said ultrasonic shock wave generating means so that said ultrasonic shock wave emitted from said ultrasonic shock wave emitting elements avoids said pulmonary alveolus.

3. An ultrasonic therapeutic apparatus as recited in claim 2, wherein said means for detecting a pulmonary alveolus comprises:
   (1) a high frequency pulse generator circuit for applying a high frequency pulse to said ultrasonic shock wave generating means to generate an ultrasonic observation wave;
   (2) a receiver circuit for receiving said ultrasonic observation wave after it has been reflected from said area within said patient's body; and
   (3) a decision circuit for:
      (i) comparing the intensity of said reflected ultrasonic observation wave to a reference intensity to determine whether a pulmonary alveolus is present; and
      (ii) generating an output signal indicating whether a pulmonary alveolus is present based upon said comparison, said output signal controlling said ultrasonic shock wave generating means so that only said ultrasonic shock wave emitting elements which are not aimed at said pulmonary alveolus are driven.

4. An ultrasonic therapeutic apparatus as recited in claim 1, wherein said means for continuously providing a location signal also determines a crushing procedure for crushing said calculus.

5. An ultrasonic therapeutic apparatus as recited in claim 1, wherein said focal point shifting means includes:
   (1) a drive unit for moving said shock wave generating means; and
   (2) a water bag which is capable of being interposed between said shock wave generating means and said patient's body.

6. An ultrasonic therapeutic apparatus as recited in claim 1, wherein said focal point shifting means comprises a shock wave inflector disposed within a bag filled with a first shock wave transmitting liquid, said bag being interposed between said shock wave generating means and said patient's body, said inflector including a flexible vessel in the form of a lens and replaceably filled with a second shock wave transmitting liquid, said second liquid having an acoustical impedance which is different from the acoustical impedance of said first shock wave transmitting liquid.

7. An ultrasonic therapeutic apparatus as recited in claim 1, wherein said focal point shifting means includes:
   (1) a cylinder located in front of said shock wave generating means, said cylinder having an open end;
   (2) a pouch covering said open end, said pouch contacting said patient's body;
   (3) an internal space defined by said cylinder and said pouch, said space being filled with a shock wave transmitting liquid; and
   (4) a plurality of vanes disposed inside of said cylinder for controlling the travelling direction of said shock wave.

8. An ultrasonic therapeutic apparatus as recited in claim 1 wherein said focal point shifting means includes:
   (1) a vessel containing a shock wave transmitting liquid, said vessel being adapted to be interposed between said patient's body and said shock wave generating means; and
   (2) a shock wave inflector disposed within said vessel, said inflector including:
      (a) a flexible lens filled with a magnetic fluid, said magnetic fluid having an acoustical impedance different from the acoustical impedance of said shock wave transmitting liquid; and
      (b) a magnet for moving said magnetic fluid to change the configuration of said inflector.

9. An ultrasonic therapeutic apparatus as recited in claim 1, wherein said focal point shifting means includes:
   (1) a vessel containing a first shock wave transmitting liquid, said vessel being adapted to be interposed between said patient's body and said shock wave generating means; and
   (2) a shock wave inflector located within said vessel, said inflector including a lens filled with a shock wave transmitting agent, said agent having an impurity, said agent having an acoustical impedance which is different from the acoustical impedance of said first liquid, said agent being replaceably charged into said flexible vessel so as to permit the amount or type of said agent to be changed.

10. An ultrasonic therapeutic apparatus as recited in claim 1, wherein said array of ultrasonic shock wave emitting elements are secured to a spherical mounting plate.

11. An ultrasonic therapeutic apparatus as recited in claim 1, wherein said observation means includes juxtaposed probes, each of said probes including ultrasonic vibrators arranged along a line.

12. An ultrasonic therapeutic apparatus as recited in claim 11, wherein each of said probes has a longitudinal axis, said observation means further including rotating means for rotating each of said probes around its longitudinal axis.

13. An ultrasonic therapeutic apparatus as recited in claim 12, wherein said rotating means includes:
(a) a pulley; and
(b) a motor for reversibly operating said pulley.

* * * * *

UNITED STATES PATENT AND TRADEMARK OFFICE
CERTIFICATE OF CORRECTION

PATENT NO. : 4,958,639
DATED : Sep. 25, 1990
INVENTOR(S) : Naoki Uchiyama et al.

It is certified that error appears in the above-identified patent and that said Letters Patent is hereby corrected as shown below:

Title page:
In the statement of the Foreign Application Priority Data, the fourth listed Japanese patent application serial number should read --61-282980--.

Signed and Sealed this

Twenty-third Day of June, 1992

Attest:

DOUGLAS B. COMER

*Attesting Officer*   *Acting Commissioner of Patents and Trademarks*